United States Patent [19]

Naylor et al.

[11] 4,096,175

[45] Jun. 20, 1978

[54] EXTRACTION METHOD

[75] Inventors: Carter G. Naylor; Simon P. Burns, both of Austin, Tex.

[73] Assignee: Texaco Development Corporation, New York, N.Y.

[21] Appl. No.: 746,648

[22] Filed: Dec. 1, 1976

[51] Int. Cl.$^2$ .......................................... C07C 143/42
[52] U.S. Cl. ............................ 260/512 R; 260/513 R; 260/612 D; 260/613 B; 260/615 B; 568/756; 568/780; 568/708; 568/755; 568/868; 568/913; 568/920

[58] Field of Search .......... 260/512 R, 513 R, 643 D, 260/621 A, 624 A, 613 B, 615 B, 637 R

[56] References Cited

U.S. PATENT DOCUMENTS 2,241,421  5/1941  Price et al. ..................... 260/513 R
2,535,678  12/1950  Hollander et al. ............... 260/512 R

*Primary Examiner*—Nicky Chan
*Attorney, Agent, or Firm*—Carl G. Ries; Thomas H. Whaley; James L. Bailey

[57] ABSTRACT

Covers a method of separating a nonionic surfactant from an anionic surfactant by use of methylal.

4 Claims, No Drawings

EXTRACTION METHOD

BACKGROUND OF THE INVENTION

1. Field of the Invention

This invention relates to a method of extracting out certain sulfonated organic compounds from alcohols used to prepare said compounds.

2. Description of the Prior Art

Organic sulfonic acids and organic sulfonates are becoming increasingly important due to their use in the preparation of liquid detergents, as surfactants for enhanced oil recovery processes and for other uses. A number of general schemes are available to sulfonate organic compounds. For example, sulfonated materials may be prepared by sulfonation processes employing concentrated sulfuric acid or oleum. Another method of preparing organic sulfonates involves reacting an organic alcohol containing at least one hydroxyl group with a hydroxy-containing alkyl sulfonic acid or salt thereof. Under appropriate conditions the two compounds are condensed with formation of by-product water to produce an ether sulfonate. This reaction can be termed a sulfoalkylation reaction. A typical sulfonating reagent here used to react with a wide variety of organic alcohols is sodium isethionate, also named as the sodium salt of 2-hydroxy ethane sulfonic acid.

In most instances it is necessary to separate out the sulfonate produced or anionic surfactant from the reaction mixture which normally contains unreacted starting materials such as the alcohol reactant. In the above case wherein an alcohol is reacted with a sulfonating agent such as sodium isethionate usually an excess of alcohol is employed to assist in driving the reaction to completion. Thus, it is necessary to resolve the mixture of starting alcohol material and final ether sulfonate, one from the other.

There are a number of ways available to effect such separation. However, with respect to surfactants of relatively high molecular weight usually an extraction technique is devised. The use of such extractants in the usual situation is at best an emperical type of science faced with much unpredictability. For example, a class of extractant materials useful in separating one group of nonionic surfactants from anionic surfactants derived therefrom may be entirely useless in making a similar resolution, though of only a slightly different class of surfactants.

In other situations while a solvent may be found useful as an extractant in certain situations, such solvent while displaying proper selectivity may have other drawbacks such as itself being unstable, or having a tendency to convert the materials being separated to other derivatives by chemical reaction, which derivatives may be corrosive or have other undesirable properties. In still further instances, the extraction may require heat, causing formation of emulsions or gels. Lastly, while a solvent may be useful as an extractant, in many instances the solvent itself is difficult to separate out from the material it has extracted, and in some cases is impossible to do so.

It is therefore a principle object of this invention to provide a method for separating out ether sulfonates from organic alcohols from which ether sulfonates were derived through reaction with hydroxy-containing alkyl sulfonic acids or salts by means of a unique extraction technique, which process is free from the just-mentioned disadvantages of prior art processes.

The above-mentioned object and advantages of the present invention will become apparent as the invention is more thoroughly discussed hereinafter.

SUMMARY OF THE INVENTION

In its broadest aspects the present invention comprises a method of resolving a mixture of a nonionic surfactant and an anionic surfactant existing in an aqueous medium, said nonionic surfactant having a structural formula as follows:

where $R_2$ is a radical selected group consisting $C_1-C_{22}$ alkyl, $C_1-C_{22}$ alkenyl, $C_1-C_{22}$ hydroxy alkyl, $C_1-C_{22}$ hydroxy alkenyl, alkaryl containing one or more $C_1-C_{22}$ groups substituted on said aryl group, aralkyl containing 7-22 carbon atoms, and polyether derivatives of any of the foregoing, with said anionic surfactant having a structural formula as follows:

where $R_2$ has a significance as above, $R_3$ is alkylene or arylene and A represents an cation; which comprises the step of treating said aqueous media with at least an effective amount of methylal sufficient to dissolve said nonionic surfactant in said methylal and separating out said solution or nonionic surfactant in methylal from a remaining solution or anionic surfactant in water.

A DESCRIPTION OF THE PREFERRED EMBODIMENTS

In more detail the practice of the present invention relates to a method of separating out nonionic surfactant alcohols of the above type from anionic sulfonate surfactants prepared therefrom. The ether sulfonates which are derived from the alcohol surfactants are prepared by reacting said alcohol compound with a hydroxy-containing alkyl sulfonic acid or salt thereof. The sulfonation reaction may be carried out via a number of prior art techniques, which will not described in any detail since their description forms no part of the invention.

A number of alcohols, $R_2OH$, may be resolved via the process here from ether sulfonates formed therefrom. Such alcohols may include methanol, ethanol, isopropanol, n-propanol, t-butanol, isobutanol, n-butanol, heptyl alcohol, hexyl alcohol, fatty alcohols containing from about 8 to about 20 carbon atoms such as octyl alcohol, decyl alcohol, lauryl alcohol, tridecyl alcohol, tetradecyl alcohol, cetyl alcohol, tallow alcohol, octadecyl alcohol, and eicosyl alcohol.

Other alcohols which may be treated here include the so-called Oxo alcohols from the Oxo process, vinylidene alcohols, Ziegler-type primary linear alcohols prepared from trialkylaluminum mixtures made by way of ethylene polymerization, subsequent oxidation, and hydrolysis of the resultant aluminum alkoxides as set out in U.S. Pat. No. 3,598,747, and other alcohols of this type. Typical vinylidene alcohols are set out in U.S. Pat. No. 3,952,068 and have the general structure

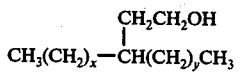

wherein individually, x and y are numbers from 1 to 15 and the sum of x and y is in the range of 6 to 16.

Polyhydric alcohols may also be included in the process of the invention, including such polyhydric alcohols as aliphatic polyhydric alcohols including the aliphatic glycols, such as, for example, ethylene glycol, propylene glycol, butanediol-1, 4 etc.; and the glycol ethers such as diethylene glycol, dipropylene glycol and the like. Higher functionality polyhydric materials which may be treated include such as glycerol, sorbitol, trimethylolpropane, 1,2,6-hexanetriol, pentaerythritol and the like. Also, suitable are dihydric aromatic materials such as bisphenol-A and hydrogenated bisphenol-A. Preferred polyhydric alcohols are the aliphatic glycols having from 2 to 10 carbon atoms and the aliphatic glycol ethers having from 4 to 20 carbon atoms.

Still other alcohols which may be separated from their ether sulfonates include alkylene glycol monolower alkyl ether compounds such as ethylene glycol monomethyl ether, ethylene glycol monobutyl ether (Butyl Cellosolve), propylene glycol monomethyl ether, propylene glycol monoethyl ether, diethylene glycol monobutyl ether (Butyl Carbitol), and the like.

Phenols and alkyl substituted phenols may also be employed here. Thus, for example, exemplary phenolic reactants include phenol, nonylphenol, bromophenol, iodophenol, chlorophenol, hydroxyanisole, dinonylphenol, dichlorophenol, cresol, and the like. Particularly preferred are alkyl substituted phenolic compounds falling within the following structural formula

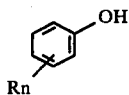

where R is an alkyl group containing from 6 to 20 carbon atoms or a halo, nitro, or hydroxy alkyl substituted group of the same chain length, and $n$ is an integer of 1, 2 or 3. Typically R in the above formula is a $C_{8-12}$ alkyl group.

Another useful class of reactant alcohols from which ether sulfonates are prepared and which can be treated here are those prepared by alkoxylating any of the above class of alcohols or others. Thus, the above compounds may be reacted with ethylene oxide, propylene oxide, butylene oxide or higher alkylene oxides having up to 18 carbon atoms or mixtures thereof. When mixed oxides are used, they may be added to the hydroxy or polyhydroxy compound either sequentially to form block polyether polyol compounds, or may be mixed and reacted simultaneously to form a random, or heteric oxyalkylene chain. The reaction of an alkylene oxide and hydroxy or polyhydroxy compound is well-known to those skilled in the art, and the base-catalyzed reaction is particularly described in U.S. Pat. Nos. 3,655,590; 3,535,307 and 3,194,773. If diols, triols, tetrols and mixtures thereof are alkoxylated polyether polyols may be obtained which have a molecular weight of from about 500 to about 10,000. These polyether polyols are well-known and may be prepared by any known process such as, for example, the processes described in Encyclopedia of Chemical Technology, Vol. 7, pages 257–262, published by Interscience Publishers, Inc.

A greatly preferred class of hydroxy compounds from which ether sulfonates may be prepared include the compounds falling within the following

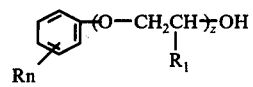

where R is a $C_1$–$C_{22}$ radical and n is an integer of 1–3, $R_1$ is hydrogen or an alkyl group of 1–18 carbon atoms, and z is a number ranging from 1 to 40. Preferably $R_1$ is hydrogen or methyl and z is 1—10.

Still other alcohols are aralkanols containing a total of from about 7 to about 28 carbon atoms. These may be represented by the following formula

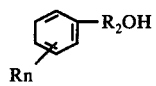

where $R_2$ is an alkylene group containing 1–22 carbon atoms, and R and n are as just noted. Polyether derivatives of these compounds may also be made by appropriate alkoxylation techniques.

Thus, preferred alcohols which may be employed as reactants in preparing ether sulfonates and thus must be separated therefrom via the process here are those having the general formula ROH, where R is a radical selected from the group consisting of $C_1$–$C_{22}$ alkyl, $C_1$–$C_{22}$ alkenyl, hydroxy or polyhydroxy derivatives of these alkyl or alkenyl compounds, alkaryl radicals containing one or more $C_1$–$C_{18}$ alkyl groups substituted on said aryl group, and aralkyl radicals containing 7–22 carbon atoms, and polyether derivatives of any of the foregoing.

Ether sulfonates are then prepared from the above alcohols. The sulfonating agent (sulfoalkylating agent) preferably used is a hydroxyalkyl sulfonic acid or salt thereof. Preferably, the sulfonating agent is an alkali or alkaline earth metal hydroxy-terminated straight chain alkyl sulfonic acid or salt. Thus, the sulfonating agent employed here has the following structural formula $$OHR_3SO_3A$$

where $R_3$ is a straight or branched alkylene group or an arylene group such as phenylene, which optionally may contain other non-interfering groups such as halo, nitro, nitrile, etc. groups. More preferably, $R_3$ is a straight or branched chain unsubstituted alkylene group such as methylene, ethylene, propylene, butylene, pentylene, hexylene and higher alkylene groups. Most preferably, $R_3$ contains 1–4 carbon atoms, and in a greatly preferred embodiment is ethylene or propylene. A represents hydrogen or a cation, preferably an alkali or alkaline earth metal cation such as sodium, lithium, potassium, calcium, magnesium, cesium, etc.

In the most preferred embodiment of the invention, a process of separating ether sulfonates of the formula

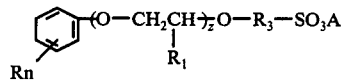

from alcohols formed therefrom is carried out. Here R is a $C_1$–$C_{22}$ alkyl group, $n$ is an integer of 1–3, $R_1$ is hydrogen or methyl, z is an integer of 1–40, $R_3$ is ethylene or propylene and A is hydrogen or an alkali or alkaline earth metal cation. More preferably A is an alkali or an alkaline earth cation, and most preferably is an alkali metal cation as sodium or potassium. In this instance an alcoholic compound of the formula

when R, $n$, $R_1$ and $z$ have a significance as just discussed is reacted with a compound of the formula

OHR$_3$SO$_3$A where $R_3$ and A are as just mentioned. The product ether sulfonate is then separated from the reactant alcohol by the extraction technique used here.

The extraction practice here itself utilizing methylal (dimethoxymethane) is carried conventionally. One or more extractions may be effected. Moreover, the extraction may be carried at room temperature or even below as it may likewise be done at temperatures of say 40–80° C. The methylal extractant will selectively remove the alcohol ether sulfonate at temperatures up to the boiling point of the extraction mixture. Again, the extraction method may be employed at atmospheric, sub-atmospheric or super-atmospheric pressures. By contact of the mixture of alcohol and ether sulfonate with methylal, the methylal selectively acts as a solvent for the nonionic surfactant alcohol while the anionic sulfonate stays behind in the aqueous media. The methylal may be then distilled from the alcohol while the ether sulfonate may be recovered from the aqueous phase by a number of techniques including distillation off of water, precipitation, crystallation or through other means.

The following examples specifically illustrate the process of the invention. It should be understood of course, that these are merely illustrative and that the invention is not to be limited thereto.

EXAMPLE I

Here 40 grams of an aqueous slurry of approximately equal amounts of the alcohol

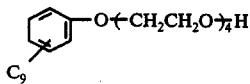

and an ethoxy sulfonate having the structure

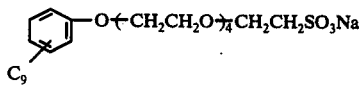

were extracted with 240 gram portions of methylal. The aqueous layer was analyzed for alcohol and anionic surfactant and found to contain 0.7 grams of alcohol and 4.84 grams of the ethoxy sulfonate anionic surfactant.

EXAMPLE II

Here an aqueous mixture (20% solids) of the alcohol of Example I (7.94%) and the ether sulfonate of Example I (9.7%) in an amount of 2,000 grams was extracted sequentially with 1,500 grams of methylal followed by 6 extractions using 500 grams of methylal. The combined organic extracts were distilled to yield 165.6 grams of residue which contain approximately 16 grams of ether sulfonate. The aqueous layer was stripped of dissolved methylal to give 1538 grams of a solution containing 11.0% ether sulfonate and 0.25% alcohol. Results of this experiment are summarized below.

TABLE I

| MIXTURE COMPONENT | CRUDE MIXTURE | AQUEOUS LAYER | METHYLAL EXTRACT |
|---|---|---|---|
| Alcohol | 159 grams | 3.8 grams | not analyzed |
| Ether Sulfonate | 189 grams | 169 grams | 16 grams |

EXAMPLE III

In this run 100 grams of an aqueous slurry (48.5% water) of an alcohol (24.8%) having the formula

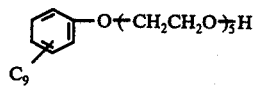

and an ether sulfonate (20.5%) having the formula

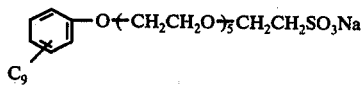

were extracted in a separatory funnel with 100 grams of water and 200 grams of methylal followed by extraction with a second 200 gram portion of methylal, and finally with 100 grams of methylal. The combined extracts were evaporated to give 23.7 grams of residue. The aqueous layer was stripped to give 146 grams of solution containing 13.1% ether sulfonate and 1.32% alcohol. Results of this run are given below:

TABLE II

| MIXTURE COMPONENT | CRUDE MIXTURE | AQUEOUS LAYER | METHYLAL EXTRACT |
|---|---|---|---|
| Alcohol | 24.8 grams | 1.9 grams | Not analyzed |
| Ether Sulfonate | 20.5 grams | 19.2 grams | 0.5 grams |

EXAMPLE IV

The efficiency of the methylal as an extractant in the particular system here was compared with a number of other solvents by mixing 10 grams of crude aqueous ether sulfonate of Example I (30% solids) and 10 grams of solvent. Results are given in Table III below. While ethyl acetate may act as a solvent in the system treated by the process of the invention, use of ethyl acetate has a number of drawbacks. For example, such solvent has a higher boiling point than methylal and is not as easily recovered by distillation. In addition, to avoid emulsions and gels use of ethyl acetate requires heating, leading to the tendency therefore to convert it to ethanol and acetic acid causing transesterification of the alkoxylate being separated out. Also, the acetic acid formed is corrosive to equipment and the ethanol detracts from the extraction properties of ethyl acetate.

As can be seen from Table III below normally methylal and ethyl acetate have the ability to function as an extraction solvent in removing alcohols from ether sulfonates formed therefrom. However, as just noted, ethyl acetate has a number of glaring deficiencies which make it less attractive than use of the methylal solvent.

TABLE III

| SOLVENT | APPEARANCE OF SOLUTION |
| --- | --- |
| Ethyl Acetate | Two layers of about equal volume |
| Methylal | Two layers of about equal volume |
| Acetone | Clear solution with trace of sediment. |
| Methyl Ethyl Ketone | Clear solution |
| 2-Propanol | Clear solution |
| 2-Butanol | Small lower layer, about 5% of total volume |
| Butyl Acetate | Emulsion |
| Butylal | Emulsion |
| Hexane | Gel |
| Tetrahydrofuran | Clear solution |

The terms "sulfonation" and "sulfonating agent" as herein used are meant to refer to and include both situations involving a convention sulfonation reaction and a sulfoalkylation reaction.

The invention is hereby claimed as follows:

We claim:

1. The method of resolving a mixture of a nonionic surfactant and an anionic surfactant existing in an aqueous medium, said nonionic surfactant having a structural formula as follows:

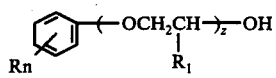

where R is a $C_1$–$C_{22}$ alkyl group, $n$ is an integer of 1–3, $R_1$ is H or $CH_3$, and $z$ is an integer of 1–40, said anionic surfactant having a structural formula as follows:

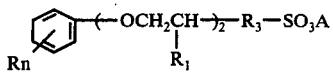

where R, $R_1$, $n$ and $z$ have a significance as above, $R_3$ is ethylene or propylene and A is an alkali metal cation which comprises the step of treating said aqueous mixture with at least an effective amount of methylal sufficient to dissolve said nonionic surfactant in said methylal and separating out the methylal phase containing the nonionic surfactant from the aqueous phase containing the anionic surfactant.

2. The method of claim 1 wherein said treatment is carried out at room temperature.

3. The method of claim 1 wherein methylal is separated from the nonionic surfactant in the methylal phase by distilling out the methylal.

4. The method of claim 1 where $R_3$ is ethylene.

* * * * *